(12) United States Patent
Moore et al.

(10) Patent No.: US 6,495,595 B2
(45) Date of Patent: Dec. 17, 2002

(54) PESTICIDE FORMULATIONS CONTAINING ALKOXYLATED TRISTYRYLPHENOL HEMI-SULFATE ESTER NEUTRALIZED ALKOXYLATED AMINE SURFACTANTS

(75) Inventors: Carolyn Estep Moore, Kernersville, NC (US); Victor Shui-Chiu Chow, Jamestown, NC (US); Michael James Hopkinson, Pleasant Garden, NC (US); Tammy Tyler Shannon, Winfield, WV (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/881,414

(22) Filed: Jun. 14, 2001

(65) Prior Publication Data

US 2002/0058697 A1 May 16, 2002

Related U.S. Application Data

(63) Continuation of application No. PCT/EP99/09869, filed on Dec. 13, 1999.

(51) Int. Cl.⁷ .............................................. A01N 41/00
(52) U.S. Cl. .............................. 514/517; 558/26; 558/27
(58) Field of Search ............................. 558/26, 20, 27; 514/717, 718, 517; 504/345

(56) References Cited

FOREIGN PATENT DOCUMENTS

| EP | 0 177 111 A2 | 4/1986 |
|----|----|----|
| EP | 0 500 401 A1 | 8/1992 |
| WO | WO 95/17087 | 6/1995 |
| WO | WO 97/40669 | 11/1997 |

OTHER PUBLICATIONS

CA:127:201436 abs of JP09208404 Aug. 1997.*
CA:106:86178 abs of JP 61213273 Sep. 1986.*

* cited by examiner

*Primary Examiner*—Jean F. Vollano
(74) *Attorney, Agent, or Firm*—William A. Teoli, Jr.; Thomas Hamilton

(57) ABSTRACT

The present invention relates to a surfactant for general use in agricultural compositions, including, but not limited to herbicidal, fungicidal and insecticidal formulations comprised of two components: an alkoxylated tristyrylphenol acid neutralized to the desired pH or properties with an appropriate amount of alkoxylated alkyl amine.

27 Claims, No Drawings

PESTICIDE FORMULATIONS CONTAINING ALKOXYLATED TRISTYRYLPHENOL HEMI-SULFATE ESTER NEUTRALIZED ALKOXYLATED AMINE SURFACTANTS

This application is a continuation of International Application No. PCT/EP99/09869, filed Dec. 13, 1999, the contents of which are incorporated herein by reference, which claims priority to U.S. Ser. No. 09/211,062, filed Dec. 14, 1998, now abandoned.

FIELD OF THE INVENTION

The present invention relates to a surfactant system for general use in agricultural compositions, including, but not limited to herbicidal, fungicidal and insecticidal formulations comprised of two components: an alkoxylated tristyrylphenol hemi-sulfate ester neutralized to the desired pH with an appropriate amount of an alkoxylated alkyl amine.

BACKGROUND OF THE INVENTION

Alkylphenol ethoxylates (APE's) and their anionic derivatives are surfactants that are well known to industry and have historically been relied upon heavily by agricultural chemical producers. However, formulations containing APEs do not always provide the most desirable combination of design specifications, e.g. product efficacy, working parameters and cost. Traditional non-APE surfactant systems have not been readily adaptable substitutes for APE surfactants. For example, calcium dodecylbenzene sulfonic acid used in conjunction with alkoxylated amines have not been as robust as the APE's and their derivatives due to unacceptable performance in one or more key performance areas, such as emulsion stability, acute toxicity, temporal and thermal stability, chemical and physical stability; solution, suspension or dilution dynamics; shear stress tolerance; viscosity; or lack of compatibility with mixing partners.

Phosphate esters of alcohol ethoxylates, which are non-APE surfactants found in many industrial uses, have long term stability problems due to hydrolytically driven transesterification and saponification reactions involving the mono-ester, di-ester, and free acid components of the surfactant mixture. Sulfated surfactants in flowable formulations are typically prone to hydrolytic decomposition, particularly when the formulations are stored in hot, summer warehouse conditions. Thus, there has been a need for an alternative surfactant system which could be easily made from readily available and cost effective raw materials and would be robust to chemical and physical conditions which might be encountered by the formulated product in its life span.

SUMMARY OF THE INVENTION

Surprisingly, it has now been discovered that certain aromatic acids such as alkoxylated tristyrylphenol hemi-sulfate esters which have been neutralized with alkoxylated amines are suitable as alternative ionic surfactants for general use in agricultural products. Even though ethoxylated tristyrylphenol hemi-sulfate esters fall into the general classification of APE's, the tristyrylphenol group is structurally very different from known or conventional APE surfactants. The surfactants of the instant invention may be in the form of a surfactant compound, or composition containing one or more the surfactant compounds or salts. In one embodiment of the invention, the compositions containing the instant surfactant compounds do not contain or are substantially free of known or conventional APEs. The surfactants of the instant invention are obtained from combining the appropriate alkoxylated tristyrylphenol hemi-sulfate ester with the appropriate alkoxylated amine.

The steric configuration of the tristyrylphenol group protects the surfactant from hydrolytic cleavage typically observed in other known anionic sulfate ester surfactant systems.

DETAILED DESCRIPTION OF THE INVENTION

One aspect of the invention concerns the compounds of Formula (1):

$$(H\text{-}B)^+ A^- \tag{1}$$

wherein $A^-$ is the conjugate base of the acid H-A, wherein H-A is an alkoxylated tristyrylphenol hemi-sulfate ester; and the $(H\text{-}B)^+$ is the conjugate acid of the base B, wherein B is an alkoxylated amine. A preferred aspect of the invention are the compounds having the formula $(H\text{-}B)^+ A^-$, where $A^-$ is the anion of the formula:

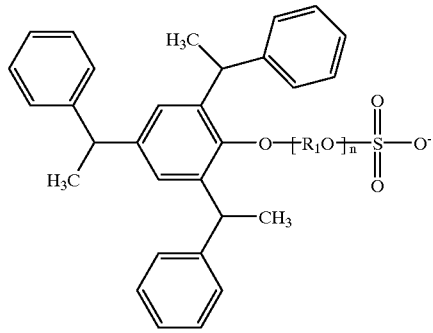

wherein each $R_1$ independently is a straight chain or branched $C_2$-$C_4$ alkylene, n is a number from 1 to 50 inclusive, and wherein $(H\text{-}B)^+$ is the cation of the formula:

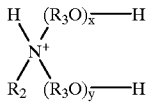

wherein $R_2$ is selected from the group consisting of hydrogen, $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive. "Independently" in the context of the $R_3$ definition means that $R_3$ may be selected independently in all respects. Thus, the substituents —$(R_3O)_x$—H and —$(R_3O)_y$—H as a whole may be composed of different $R_3$ groups, and each of the substituents themselves also may be composed of different $R_3$ groups.

A more preferred embodiment of the invention are the compounds of formula (1) wherein $A^-$ is:

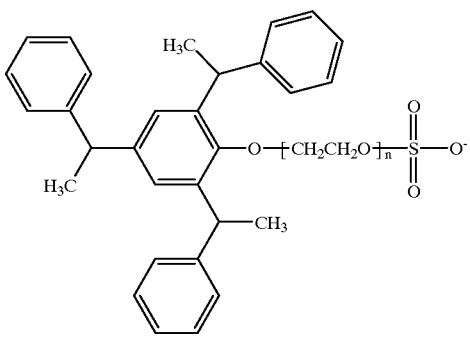

wherein n is from about 4 to 25 (preferably 4 to 16, especially 8); and wherein $(H-B)^+$ is the cation of the formula:

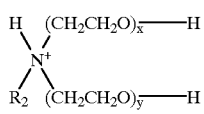

wherein $R_2$ is selected from the group consisting of n-octadecyl, n-hexadecyl and cis-9-octadecenyl, and x+y is a number from about 2 to 15 (preferably 4 to 9). A feature of the invention is where x+y is 5.

The invention also concerns the compound or salt produced from the process of neutralizing an alkoxylated tristyrylphenol hemi-sulfate ester of formula (2) infra (also referred to as HA) with an alkoxylated amine of formula (3) infra (also herein referred to as B). The ammoniumsulfate compounds or the product from the process of combining an aromatic acid HA with an alkoxylated amine B (to the extent there is a difference) are both features of the instantly disclosed invention. The scope of the invention disclosed herein should not be construed to be limited by any particular chemical theory relating to the complexation, equilibration, reaction or acid-base chemistry of the components used to make the surfactants or other ingredients used to make other ultimately useful formulations such as, pesticide formulations. In this regard, another aspect of the invention is the surfactant composition comprising one or more aromatic acids and one or more alkoxylated amines wherein the constituent components may or may not have interacted chemically so as to result in a change in form of the components. The invention encompasses the static composition of the appropriate components admixed together as well as the chemically integrated surfactant composition comprising at least one aromatic acid and at least one alkoxylated amine. "Static composition" denotes the composition composed of components wherein the components have not substantially changed by virtue of their combination with other composition components. "Chemically integrated composition" means a composition that results from the natural equilibration, complexation, dissociation or other chemical transformation if any that may occur after combination of the components and prior to ultimate use of the surfactant in a pesticide formulation. Therefore, the "chemically integrated composition" of the instant invention by definition encompasses the situation where there is a "static composition" as well as any resultant composition occurring at any point in time between initial creation and ultimate use in the field of products containing the surfactant. In other words, the disclosed invention is not limited to a static composition of chemically unaltered constituent components.

Another aspect of the invention is the surfactant composition produced as a whole from the combination of the aromatic acid HA and the alkoxylated amine base B to the extent it is composed of products other than ammoniumsulfate compounds. Such a composition may contain chemically unaltered starting materials as well as other reaction products or by-products from reaction, equilibration, dissociation or complexation of the components in the composition.

The invention also includes the process for obtaining a surfactant which is useful as a substitute for known or conventional APE's. In addition to the surfactant product or the product-by-process, the process of obtaining or making any of the surfactants is herein disclosed as part of the invention. The invention also includes the method of using the surfactant compounds of formula (1) and compositions thereof as substitutes for known or conventional APEs.

The alkoxylated amines B and the aromatic acids HA used to make the surfactants of the invention are preferably those compounds that are readily available and inexpensive. However, cost of materials is only one factor in selecting specific alkoxylated amines B and aromatic acids HA used as starting materials. After performing a routine cost-benefit analysis and in view of other design parameters it may become apparent that more expensive and less readily available starting materials may be preferred.

The aromatic acids used in the instant invention may generally be defined by formula (2):

(2)

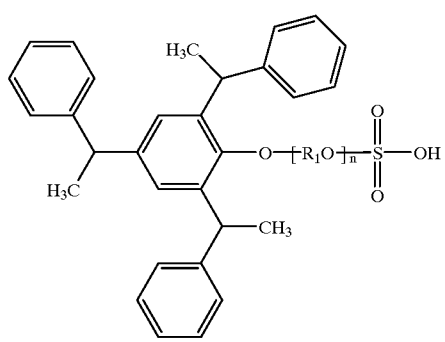

wherein each $R_1$ independently is a straight chain or branched $C_2$-$C_4$ alkylene, and n is a number from 1 to 50 inclusive.

The preferred starting materials for making the surfactants of the instant invention are one or more of the compounds defined by formula (2a):

(2a)

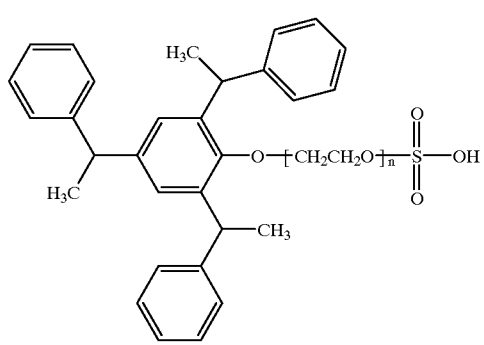

wherein n is defined as above.

The preferred alkoxylated amines useful for making the surfactants of the instant invention are one or more of the compounds defined by formula (3):

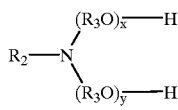
(3)

wherein $R_2$ is selected from the group consisting of hydrogen, $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive. A preferred feature of the invention is where the alkoxylated amines are one or more of the ethoxylated amines of formula (3a):

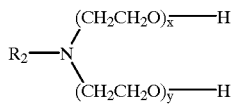
(3a)

wherein $R_2$, x and y are defined above, preferably wherein $R_2$ is $C_1$-$C_{24}$ alkyl and the average of x+y is a number from about 2 to 15. Additional preferred aspects of the invention are where $R_2$ is selected from the group consisting of n-octadecyl, n-hexadecyl and cis-9-octadecenyl, and x+y is a number from 4 to 9. A feature of the invention is where the average value of x+y is 5.

Another aspect of the invention is the composition comprising the formulation of the surfactants disclosed above in formulations that contain one or more other active ingredients. A preferred embodiment of the invention is a pesticide formulation which contains the presently disclosed surfactants. However, the invention is not limited to pesticide formulations. Other useful formulations that may contain the instantly disclosed surfactants include shampoo formulations, detergent formulations generally and soap formulations used in the mining industry. The surfactants presently disclosed are considered to have of general applicability as alternatives to conventional APE's, and therefore would be expected to be useful in many other known formulations. The invention encompasses any formulation obtained by otherwise substituting the instantly disclosed surfactants as alternatives to known APEs surfactants as well as other surfactants. The instantly disclosed invention also encompasses any formulation obtained by supplementing compositions containing known or conventional APEs with the instantly claimed surfactants. Generally, any formulation that makes use of a surfactant additive would be subject to modification by substitution or supplementation with one or more of the surfactants of the instant invention. Although the compounds and compositions are referred to as "surfactants" in the instant application, it is expected that they will also have other nonsurfactant properties that may be useful independently of any inherent surfactant properties. Depending on the application of the instant invention, it may result in increased bioefficacy and/or reduced toxicity and irritation.

Another aspect of the invention is the composition comprising the formulation of the surfactants disclosed above in formulations that contain one or more herbicides and one or more safeners (antidotes). When applying herbicides, the cultivated plants may also suffer severe damage owing to factors that include the concentration of the herbicide and the mode of application, the cultivated plant itself, the nature of the soil, and the climatic conditions such as exposure. A preferred embodiment of the invention is for example the formulation of the s-metolachlor and benoxacor, or s-metolachlor, atrazine and benoxacor each in combination with the surfactants of the instant invention.

The surfactants are prepared by mixing at least one aromatic acid of formula (2) with at least one alkoxylated amine of formula (3) while controlling pH. The desired pH is maintained by precisely regulating the ratio of the acid and base components in the composition. For example, the appropriate acid-base ratio and desired pH can be achieved according to the following procedure: 1) A known weight of the aromatic acid is dissolved in a 50/50 solution of isopropanol and water. 2) A tared amount of alkoxylated amine is slowly added to the aromatic acid with constant stirring using a magnetic stirrer while pH is monitored by use of a pH meter fitted with a silver chloride electrode. 3) When the desired pH is attained, the amount of required alkoxylated amine is measured. 4) The ratio of aromatic acid: alkoxylated amine (acid: base) is determined and the surfactant is prepared by mixing the appropriate amounts of the two components with stirring. For many of the pesticide formulations described herein the preferred acid : base ratio is approximately 35:65 (weight ratio). The acidity or basicity of the constituent components may vary depending on the supplier of the materials or the particular batch, therefore the pH is the controlling factor in preparing the compounds, compositions and formulations of the instant invention. The $pK_a$ and $pK_b$ for the aromatic acid and the alkoxylated amine respectively may be varied to some extent by manipulating the type and degree of substitution for the compounds defined by formula (2) and (3). Therefore, the selection of the particular acid or base used will also effect the acid : base ratio used to make the surfactants as well as the desired pH. A preferred pH range for the surfactant is a pH from approximately about 3 to 9, a more preferred pH range is from approximately about 3 to 8.5, and an ultimately preferred pH range is from approximately 5 to 8. It is less desirable to adjust pH after the aromatic acid and amine base components are mixed by the further addition of other acids or bases typically used to raise or lower pH because even minor amounts of additional salts can make a large difference in the observed properties of the product surfactant. It is also less desirable to have additional process steps or to have the added cost associated with purchasing, handling, storage and disposal of additional chemicals.

The emulsion stability of the ethoxylated aromatic acid, such as the ethoxylated tristyrylphenol hemi-sulfate ester of formula (2a)) neutralized with an ethoxylated tallow amine of formula (3a) is typically greatest when the "average number of ethylene oxide units" (EO) on the aromatic acid is 4 to 25 (i.e. 4 to 25EO) and when the EO on the tallow amine is 4 to 9EO. "Average" is defined as the arithmetic mean of a set of real numbers (in this case the number of ethylene oxide units in the ethoxylated aromatic acids or ethoxylated amines used to make the surfactant). Another feature of the invention is where there is a continuous and symmetrical bell curve population distribution around the EO. It also may be desirable that there be low dispersion preferably within one standard deviation (σ) of the mean (average EO).

The tristyrylphenol alkoxylates and the amine alkoxylates can be prepared using chemistry procedures well known in the art. For example, the tristryrylphenol ethoxylate can be prepared by treating tristyrylphenol with a base (e.g. sodium hydroxide) followed by addition of the desired equivalents of ethylene oxide. Tristyrylphenol is either commercially available, may be prepared by known procedures or otherwise may be prepared using conventional chemistry knowledge.

TABLE 1

Examples of some commercial suppliers and product names for the ethoxylated amines (i.e. amine ethoxylates).

| Amine ethoxylate | Supplier* | Product Name | Average Number of EO |
|---|---|---|---|
| Tallow amines | Witco | Witcamine TAM-XO (X = average number of EO) | 2, 4, 4.5, 5, 6, 7, 8, 9, 10.5 and 15 |
| Coco amines | Witco | Varonic K-2XX (XX = average number of EO) | 02, 05, 10 and 15 |
|  | Stephan | Toximul TA-X (X = average number of EO) | 2, 4, 4.5, 5, 6, 7, 8, 9, 10 and 15 |
| Oleyl amine | Witco | Varonic Q-202 | 2 |

*Addresses: See TABLE 3.

Another preferred feature of the present invention is the combination of instant compounds of formula (1) with a nonionic co-surfactant. The nonionic co-surfactants are those compounds known in the art for formulating surfactant systems. The nonionic co-surfactants include polyglycol ethers, polyglycol ether derivatives of aliphatic alcohols, cycloaliphatic alcohols, phenols, or saturated or unsaturated fatty acids. Said derivatives for example may contain 3 to 120 glycol ether groups and 8 to 30 carbon atoms in the hydrocarbon moiety. Preferred co-surfactants include for example tristyrylphenol ethoxylates (2 to 50EO, more preferably 16 to 35EO). The nonionic co-surfactants include ethyleneoxide-propyleneoxide (EO-PO) block copolymers and EO-PO block copolymer derivatives of aliphatic alcohols, cycloaliphatic alcohols or phenols (e.g butoxy EO-PO block copolymers).

One preferred aspect of the invention includes the combination of the surfactant compositions herein with liquid pesticide compositions so as to obtain an emulsifiable concentrate formulation which can be directly mixed with water or other aqueous solutions to give an aqueous pesticide formulation without special mixing procedures.

The following examples illustrate further some of the specific features of the invention but are not intended to limit its scope. Where not otherwise specified throughout this specification and claims, temperatures are given in degrees centigrade.

TABLE 2

Examples of components that may be used to formulate the compositions of the instant invention.

| Product Name | Supplier | Description |
|---|---|---|
| Aromatic 150 | Exxon Corporation | aromatic hydrocarbon solvent |
| Pegasol R-150 | Mobil Chemical Company | aromatic hydrocarbon solvent |
| Cyclo Sol 150 | Shell Chemical Company | aromatic hydrocarbon solvent |
| Pluronic P-65 | BASF Corporation | EO-PO block copolymer |
| Toximul 8323 | Stepan Company | EO-PO block copolymer |
| Antifoam A | Dow Corning Corporation | silicone antifoaming agent |
| Y-6067 | Osi Specialties, Inc. | silicone antifoaming agent |
| Proxel GXL | Zeneca Inc. | biostatic |
| Nipacide BIT20 | Nipa Hardwicke, Inc. | biostatic |
| Renex 36 | ICI Surfactants | Tridecyl alcohol (6EO) |
| Rhodasurf BC-610 | Rhodia Inc. | Tridecyl alcohol (6EO) |
| Genopol X-060 | Clariant Corporation formerly Hoechst Celanese Corporation | Tridecyl alcohol (6EO) |
| Witconol TD-60 | Witco Corporation | Tridecyl alcohol (6EO) |
| Rhodopol 23 | Rhodia Inc. | Xanthan gum |
| Kelzan | Zeneca Inc. | Xanthan gum |

TABLE 3

Names and address of suppliers of materials.

| Supplier | Address |
|---|---|
| Witco Corporation | 5777 Frantz Road, P.O. Box 646, Dublin, Ohio 43017 |
| Stepan Company | Northfield, Illinois 60093 |
| Dow Corning Corporation | Midland, MI 48686 |
| Zeneca Inc. | Wilmington, DE 19897 |
| BASF, Corporation | Mt. Olive, NJ 07828 |
| Rhodia, Inc. | Cranbury, NJ 08512 |
| Nipa Hardwicke, Inc. | 3411 Silverside Road, 104 Hagley Bldg., Wilmington, DE 19810 |
| Osi Specialities, Inc. | Greenwich, CT 06831 |
| ICI Surfactants | Wilmington, DE 19850 |
| Clariant Corporation | Charlotte, NC 28201 |
| Shell Chemical Company | Houston, TX 77251 |
| Exxon Corporation | Houston, TX 77001 |
| Mobil Chemical Company | Houston, TX 77032 |

One preferred feature of the invention includes combining the surfactant system previously described with a nonionic co-surfactant and a liquid active ingredient to obtain an emulsifiable concentrate formulation which can be readily diluted with water or other liquid carriers requiring no special handling or mixing procedures. An example of such a formulation follows:

EXAMPLE 1

An oil base suspension concentrate containing liquid metolachlor as active ingredient was prepared according to the following formulation:

80.0% by weight metolachlor,
3.0% by weight tristyrylphenol ethyoxylate (8EO) hemi-sulfate ester neutralized with tallow amine (5EO),
3.0% by weight tristyrylphenol ethoxylate (20EO),
14.0% by weight aromatic hydrocarbon solvent.

The above ingredients were formulated as follows:

The tristyrylphenol ethoxylate (8EO) hemi-sulfate ester neutralized with tallowamine (5EO) and the tristyrylphenol ethoxylate (20EO) are charged to a vessel containing the aromatic hydrocarbon solvent and blended. The technical metolachlor is then added and blended until uniform.

It is understood that the surfactant system of the instant invention would be equally acceptable for, but not limited to, both aqueous and oil based formulations.

Another preferred aspect of the invention includes the combination of the surfactant system of the instant invention with a solid active ingredient. An example of such a formulation is as follows:

EXAMPLE 2

An aqueous suspension concentrate containing solid atrazine as active ingredient was prepared according to the following formulation:
43.5% by weight atrazine,
2.0% by weight tridecyl alcohol ethoxylate (6EO)
1.0% by weight EO-PO block copolymer
2.0% by weight tristyrylphenol ethyoxylate (8EO) hemi-sulfate ester neutralized with tallow amine (8EO),
5.0% by weight ethylene glycol, and water to make up 100%.

The above ingredients were formulated as follows: The atrazine technical is added gradually to a vessel containing the tridecyl alcohol ethoxylate (6EO), the EO-PO block copolymer, the tristyrylphenol ethoxylate (8EO) hemi-sulfate ester neutralized with tallow amine (8EO), the ethylene glycol and most of the water. The slurry is mixed until uniform and then milled to the appropriate particle size. The remaining water is added to meet assay specifications.

Another preferred aspect of the invention includes the combination of the surfactant system of this invention with a combination of solid and liquid active ingredients. An example of such a formulation is as follows:

EXAMPLE 3

An aqueous suspension concentrate containing solid atrazine and liquid metolachlor as the two active ingredients was prepared according to the following formulation:
26.1% by weight s-metolachlor
33.7% by weight atrazine
1.31% by weight benoxacor
0.4% by weight EO-PO block copolymer
0.67% by weight tridecylalcohol (6EO)
3.15%by weight tristyrylphenol ethyoxylate (8EO) hemi-sulfate ester neutralized with tallow amine (5EO)
1.5% by weight tristyrylphenol ethoxylate (35EO),
0.7% by weight antifoaming agent
0.03% by weight thickening agent, such as xanthan gum
0.03% by weight biostatic agent
1.6% by weight ethylene glycol, and water to make up 100%.

The above ingredients were formulated as follows: The atrazine technical is slowly added to a vessel containing the EO-PO block copolymer, some of the tridecyl alcohol (6EO), the biostatic agent, the antifoaming agent, most of the water, and most of the ethylene glycol. The contents of the vessel are mixed until uniform and then milled to the appropriate particle size. The thickening agent is added as a slurry with the remaining tridecyl alcohol and mixed until a uniform, stable final viscosity is reached. The assay is adjusted by the addition of water.

The s-metolachlor and benoxacor are charged to a second, heated vessel and stirred until the benoxacor dissolves and the solution becomes uniform. The solution is cooled. The tristyrylphenol ethyoxylate (8EO) hemi-sulfate ester neutralized with tallow amine (5EO), tristyrylphenol ethoxylate (35EO), the remainder of the ethylene glycol, and a small amount of water are added and stirred until uniform. The contents of both vessels are then mixed together simultaneously and the final composition is trimmed for assay.

It is again understood that such a formulation would be acceptable for, but not limited to, aqueous and oil based formulations.

As indicated above, additionally, one or more nonionic surfactant components may be used in conjunction with the surfactant composition previously described. Preferred co-surfactants are polyglycol ethers of aliphatic alcohols. In particular, the nonionic surfactants may include, but are not limited to, castor oil ethoxylates, tristyrylphenol ethoxylates, ethylene oxide/propylene oxide block copolymers, and/or ethylene oxide/propylene oxide block copolymers of aliphatic alcohols.

The crop protection compositions which are part of the instantly disclosed invention may be formulated in a form suitable for the intended application. Types of formulations include for example a flowable (FL) flowable concentrate for seed treatment (FS), wettable powder (WP), wettable dispersible granules (WDG), oil miscible flowable concentrate (OF), suspension concentrate (SC), emulsifiable concentrate (EC), liquid (L), water in oil emulsions (EW), granules (GR) water dispersible powder for slurry treatment (WS) and dry flowable (DF).

Some additional preferred embodiments of the instant invention are contained in Tables 4 and 5 below.

TABLE 4

Crop protection formulations containing surfactant, specified nonionic components and one or more active technical components.

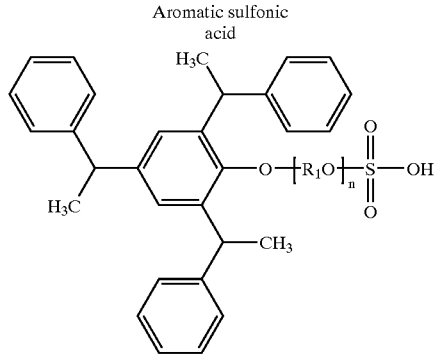

Aromatic sulfonic acid

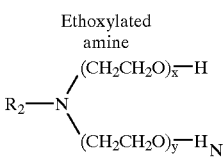

Ethoxylated amine

| $R_1$ | n | $R_2$ | $(x + y)$ | component | Active Technical $T_1$ | Active Technical $T_2$ | Active Technical $T_3$ |
|---|---|---|---|---|---|---|---|
| 1 —$CH_2CH_2$— | 8 | $C_{16-18}$ | 8 | Butoxy EO/PO block | metolachlor* | | |

TABLE 4-continued

Crop protection formulations containing surfactant, specified nonionic components and one or more active technical components.

Aromatic sulfonic acid:

$$\text{structure: trisubstituted benzene with three } \alpha\text{-methylbenzyl groups, bearing } -O-[R_1O]_n-S(=O)_2-OH$$

Ethoxylated amine:

$$R_2-N\begin{pmatrix}(CH_2CH_2O)_x-H\\(CH_2CH_2O)_y-H\end{pmatrix}$$

| # | $R_1$ | $n$ | $R_2$ | $(x+y)$ | Nonionic component | Active Technical $T_1$ | Active Technical $T_2$ | Active Technical $T_3$ |
|---|---|---|---|---|---|---|---|---|
| 2 | —$CH_2CH_2$— | 8 | $C_{12-14}$ | 3 | Butoxy EO/PO block polymer | metolachlor* | | |
| 3 | —$CH_2CH_2$— | 8 | $C_{16-18}$ | 4.5, 5, 6, 7, 8, or 9 | EO/PO block polymer | atrazine | | |
| 4 | —$CH_2CH_2$— | 8 | $C_{16-18}$ | 4.5, 5, 6, 7, 8, or 9 | ethylene glycol | atrazine | | |
| 5 | —$CH_2CH_2$— | 4 to 25 | $C_{12-14}$ | 10 | EO/PO block polymer | atrazine | | |
| 6 | —$CH_2CH_2$— | 4 to 25 | $C_{12-14}$ | 15 | EO/PO block polymer | atrazine | | |
| 7 | —$CH_2CH_2$— | 8 | $C_{16-18}$ | 4.5, 5, 6, 7, 8, or 9 | EO/PO block polymer | atrazine | | |
| 8 | —$CH_2CH_2$— | 8 | $C_{16-18}$ | 4.5, 5, 6, 7, 8, or 9 | Castor oil ethoxylate | atrazine | metolachlor* | |
| 9 | —$CH_2CH_2$— | 8 | $C_{16-18}$ | 4.5, 5, 6, 7, 8, or 9 | Butoxy EO/PO block polymer | atrazine | metolachlor* | |
| 10 | —$CH_2CH_2$— | 8 | $C_{16-18}$ | 8 | Castor oil ethoxylate | flumetralin | | |
| 11 | —$CH_2CH_2$— | 8 | $C_{16-18}$ | 8 | Castor oil ethoxylate | oxasulfuron | | |
| 12 | —$CH_2CH_2$— | 8 | $C_{16-18}$ | 8 | tristyrylphenol ethoxylate | propiconazole | | |
| 13 | —$CH_2CH_2$— | 8 | $C_{16-18}$ | 8 | Butoxy EO/PO block polymer | metribuzin | metolachlor* | |
| 14 | —$CH_2CH_2$— | 8 | $C_{12-14}$ | 3 | Butoxy EO/PO block polymer | metribuzin | metolachlor* | |
| 15 | —$CH_2CH_2$— | 8 | $C_{16-18}$ | 8 | Butoxy EO/PO block polymer | flumetsulam | metolachlor* | |
| 16 | —$CH_2CH_2$— | 8 | $C_{12-14}$ | 3 | Butoxy EO/PO block polymer | flumetsulam | metolachlor* | |
| 17 | —$CH_2CH_2$— | 8 | $C_{16-18}$ | 4.5, 5, 6, 7, 8, or 9 | Castor oil ethoxylate | flumetsulam | metolachlor* | atrazine |
| 18 | —$CH_2CH_2$— | 8 | $C_{16-18}$ | 4.5, 5, 6, 7, 8, or 9 | Butoxy EO/PO block polymer | flumetsulam | metolachlor* | atrazine |
| 19 | —$CH_2CH_2$— | 8 | $C_{16-18}$ | 8 | Butoxy EO/PO block polymer | mefenoxam | | |
| 20 | —$CH_2CH_2$— | 8 | $C_{12-14}$ | 3 | Butoxy EO/PO block polymer | mefenoxam | | |
| 21 | —$CH_2CH_2$— | 8 | $C_{16-18}$ | 8 | Butoxy EO/PO block polymer | metalaxyl | | |
| 22 | —$CH_2CH_2$— | 8 | $C_{12-14}$ | 3 | Butoxy EO/PO block polymer | metalaxyl | | |
| 23 | —$CH_2CH_2$— | 4 to 25 | $C_{16-18}$ | 4.5, 5, 6, 7, 8, | Butoxy | diazinon | | |

TABLE 4-continued

Crop protection formulations containing surfactant, specified nonionic components and one or more active technical components.

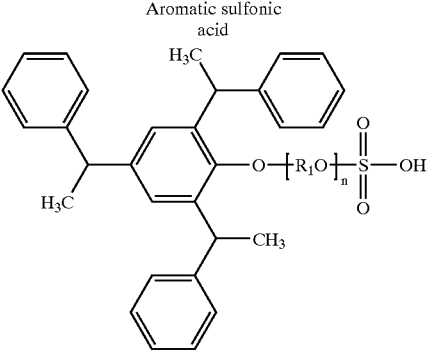

Aromatic sulfonic acid

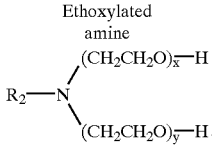

Ethoxylated amine

| R$_1$ | n | R$_2$ | (x + y) | Nonionic component | Active Technical T$_1$ | Active Technical T$_2$ | Active Technical T$_3$ |
|---|---|---|---|---|---|---|---|
| | | | | or 9 | EO/PO block polymer | | |
| 24 —CH$_2$CH$_2$— | 8 | C$_{16-18}$ | 4.5, 5, 6, 7, 8, or 9 | Butoxy EO/PO block polymer | diazinon | | |
| 25 —CH$_2$CH$_2$— | 8 | C$_{16-18}$ | 4.5, 5, 6, 7, 8, or 9 | Butoxy EO/PO block polymer | dicamba | | |
| 26 —CH$_2$CH$_2$— | 8 | C$_{16-18}$ | 4.5, 5, 6, 7, 8, or 9 | Castor oil ethoxylate | dicamba | | |
| 27 —CH$_2$CH$_2$— | 8 | C$_{16-18}$ | 4.5, 5, 6, 7, 8, or 9 | Butoxy EO/PO block polymer | COMPOUND A | | |
| 28 —CH$_2$CH$_2$— | 8 | C$_{16-18}$ | 4.5, 5, 6, 7, 8, or 9 | Castor oil ethoxylate | COMPOUND A | | |
| 29 —CH$_2$CH$_2$— | 8 | C$_{16-18}$ | 4.5, 5, 6, 7, 8, or 9 | Butoxy EO/PO block polymer | glyphosate or salts | | |
| 30 —CH$_2$CH$_2$— | 8 | C$_{16-18}$ | 8 | Butoxy EO/PO block polymer | glyphosate isopropylammonium | | |
| 31 —CH$_2$CH$_2$— | 8 | C$_{16-18}$ | 8 | Butoxy EO/PO block polymer | glyphosate sesquisodium | | |
| 32 —CH$_2$CH$_2$— | 8 | C$_{16-18}$ | 8 | Butoxy EO/PO block polymer | glyphosate trimesium | | |
| 33 —CH$_2$CH$_2$— | 8 | C$_{16-18}$ | 4.5, 5, 6, 7, 8, or 9 | Butoxy EO/PO block polymer | fluthiacet-methyl | | |
| 34 —CH$_2$CH$_2$— | 8 | C$_{16-18}$ | 4.5, 5, 6, 7, 8, or 9 | Butoxy EO/PO block polymer | glyphosate or salts | fluthiacet-methyl | |
| 35 —CH$_2$CH$_2$— | 8 | C$_{16-18}$ | 8 | Butoxy EO/PO block polymer | glyphosate isopropylammonium | fluthiacet-methyl | |
| 36 —CH$_2$CH$_2$— | 8 | C$_{16-18}$ | 8 | Butoxy EO/PO block polymer | glyphosate sesquisodium | fluthiacet-methyl | |
| 37 —CH$_2$CH$_2$— | 8 | C$_{16-18}$ | 8 | Butoxy EO/PO block polymer | glyphosate trimesium | fluthiacet-methyl | |
| 38 —CH$_2$CH$_2$— | 8 | C$_{16-18}$ | 4.5, 5, 6, 7, 8, or 9 | Butoxy EO/PO block polymer | flumiclorac-pentyl | | |
| 39 —CH$_2$CH$_2$— | 8 | C$_{16-18}$ | 4.5, 5, 6, 7, 8, or 9 | Butoxy EO/PO block polymer | glyphosate or salts | flumiclorac-pentyl | |
| 40 —CH$_2$CH$_2$— | 8 | C$_{16-18}$ | 8 | Butoxy EO/PO block polymer | glyphosate isopropylammonium | flumiclorac-pentyl | |
| 41 —CH$_2$CH$_2$— | 8 | C$_{16-18}$ | 8 | Butoxy EO/PO block polymer | glyphosate sesquisodium | flumiclorac-pentyl | |
| 42 —CH$_2$CH$_2$— | 8 | C$_{16-18}$ | 8 | Butoxy | glyphosate | flumiclorac- | |

TABLE 4-continued

Crop protection formulations containing surfactant, specified nonionic components and one or more active technical components.

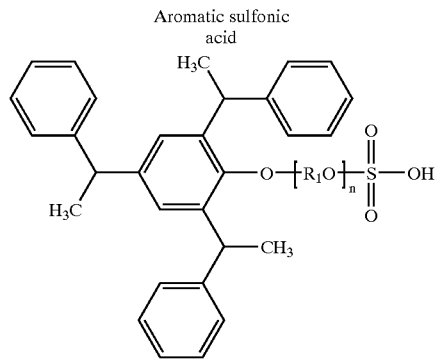

Aromatic sulfonic acid

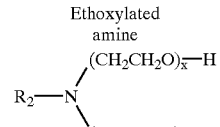

Ethoxylated amine

| | $R_1$ | n | $R_2$ | (x + y) | Nonionic component | Active Technical $T_1$ | Active Technical $T_2$ | Active Technical $T_3$ |
|---|---|---|---|---|---|---|---|---|
| | | | | | EO/PO block polymer | trimesium | pentyl | |
| 43 | —$CH_2CH_2$— | 8 | $C_{16-18}$ | 4.5, 5, 6, 7, 8, or 9 | Butoxy EO/PO block polymer | glufosinate or salts | | |
| 44 | —$CH_2CH_2$— | 8 | $C_{16-18}$ | 8 | Butoxy EO/PO block polymer | glufosinate | | |
| 45 | —$CH_2CH_2$— | 8 | $C_{16-18}$ | 8 | Butoxy EO/PO block polymer | glufosinate ammonium | | |
| 46 | —$CH_2CH_2$— | 8 | $C_{16-18}$ | 4.5, 5, 6, 7, 8, or 9 | Butoxy EO/PO block polymer | glufosinate or salts | fluthiacet-methyl | |
| 47 | —$CH_2CH_2$— | 8 | $C_{16-18}$ | 8 | Butoxy EO/PO block polymer | glufosinate | fluthiacet-methyl | |
| 48 | —$CH_2CH_2$— | 8 | $C_{16-18}$ | 8 | Butoxy EO/PO block polymer | glufosinate ammonium | fluthiacet-methyl | |
| 49 | —$CH_2CH_2$— | 8 | $C_{16-18}$ | 4.5, 5, 6, 7, 8, or 9 | Butoxy EO/PO block polymer | glufosinate or salts | flumiclorac-pentyl | |
| 50 | —$CH_2CH_2$— | 8 | $C_{16-18}$ | 8 | Butoxy EO/PO block polymer | glufosinate | flumiclorac-pentyl | |
| 51 | —$CH_2CH_2$— | 8 | $C_{16-18}$ | 8 | Butoxy EO/PO block polymer | glufosinate ammonium | flumiclorac-pentyl | |
| 52 | —$CH_2CH_2$— | 8 | $C_{16-18}$ | 8 | Butoxy EO/PO block polymer | glyphosate | atrazine | |
| 53 | —$CH_2CH_2$— | 8 | $C_{16-18}$ | 8 | Butoxy EO/PO block polymer | glyphosate | metolachlor* | atrazine |
| 54 | —$CH_2CH_2$— | 8 | $C_{16-18}$ | 8 | Butoxy EO/PO block | glyphosate salt | atrazine | |

TABLE 4-continued

Crop protection formulations containing surfactant, specified nonionic components and one or more active technical components.

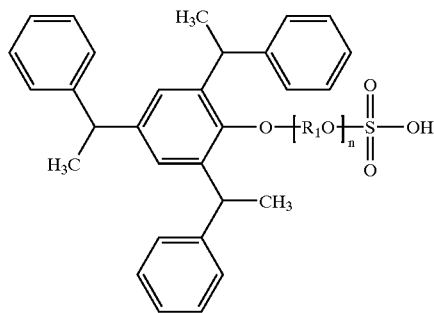

| $R_1$ | n | $R_2$ | (x + y) | Nonionic component | Active Technical $T_1$ | Active Technical $T_2$ | Active Technical $T_3$ |
|---|---|---|---|---|---|---|---|
| 55 —$CH_2CH_2$— | 8 | $C_{16-18}$ | 8 | polymer Butoxy EO/PO block polymer | glyphosate salt | metolachlor* | atrazine |

*includes the racemic mixtures or s-metolachor
x + y = EO (average # ethylene oxide units)

TABLE 5

Crop protection formulations:
Surfactant used: (defined in terms of starting materials)

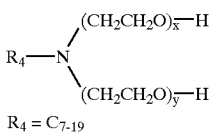

$R_1$ = $C_{2-4}$ alkylene
n = 4 to 16

$R_4$—N(CH$_2$CH$_2$O)$_{\overline{x}}$—H
     (CH$_2$CH$_2$O)$_{\overline{y}}$—H
$R_4$ = $C_{7-19}$
x + y = 2EO to 15EO Active technical ingredients used and formulation type:

| ACTIVE TECHNICAL $T_1$ | ACTIVE TECHNICAL $T_2$ | ACTIVE TECHNICAL $T_3$ | FORMULATION TYPE |
|---|---|---|---|
| Atrazine | | | FL, WP, WDG, OF |
| Atrazine | Flumetsulam | | FL, WP, WDG, OF |
| Atrazine | Metolachlor | | SC, OF, WDG |
| Atrazine | Flumetsulam | Metolachlor | SC, OF, WDG |
| Ametryn | | | OF, EC, WP, L, WDG |
| Chlorothalonil | | | FL, WDG, WP |

TABLE 5-continued

| | | |
|---|---|---|
| Chlorothalonil | Metalaxyl | EC, WDG, WP, OF |
| Cyprodinil | | EC, WP, OF, WDG |
| Cyromazine | | WP, L |
| Diazinon | | EW, W, EC, WDG |
| Dicamba | | GR, L |
| Dicamba | Prosulfuron | WDG |
| Difenoconazole | | WP, EC, WS, FS |
| Difenoconazole | Metalaxyl | WP, EC, WS, FS |
| Diofenolan | | EC, WP |
| Fenoxycarb | | WP, WDG, EC |
| Fenoxycarb | Pymetrozine | WP, WDG, EC |
| Fludioxinil | | L, FS, WDG, WP |
| Fludioxinil | Metalaxyl | L, FS, WDG, WP |
| Fludioxinil | Propiconazole | L, FS, WDG, WP |
| Flumetralin | | EC, WDG, WP |
| Flumetralin | Oxasulfuron | EC, WDG, WP |
| Flumetsulam | | EC, WDG, WP, OF |
| Flumetsulam | Metolachlor | EC, WDG, WP, OF |
| Fluometuron | | L, DF, WP |
| Fluthiacet-methyl | | EC, WDG, WP |
| Fluthiacet-methyl | Glyphosate | EC, WDG, WP |
| Fluthiacet-methyl | Oxasulfuron | EC, WDG, WP |
| Isazofos | | EC, GR |
| Mancozeb | | SC, FL, WDG, WP |
| Mancozeb | Metalaxyl | SC, FL, WDG, WP |
| Mefenoxam | | EC, WP, GR, FL, L |
| Metalaxyl | | EC, GR, L, WP |
| Methidathion | | EC, WP |
| Metolachlor | | EC, DF, GR |
| Metolachlor | Metribuzin | WDG, OF, EC |
| Metolachlor | Simazine | WDG, OF, SC |
| s-Metolachlor | | EC, DF, GR |
| s-Metolachlor | Metribuzin | WDG, OF, EC |
| s-Metolachlor | Simazine | WDG, OF, SC |
| Metribuzin | | EC, DF, WDG, OF |
| Norflurazon | | DF, GR |
| Primisulfuron | | WDG, WP |
| Primisulfuron | Prosulfuron | WDG, WP |
| Profenofos | | EC |
| Prometon | | EC, FL, OF, WP |
| Prometryn | | WP, L, OF |
| Propiconazole | | EC, WP |

TABLE 5-continued

| | |
|---|---|
| Pymetrozine | WDG, WP |
| Simazine | WP, WDG, L, GR |
| Triforine | WP, EC |
| Trinexapac-ethyl | EC, WDG, |
| COMPOUND A | WDG, OF, EC, SC |
| COMPOUND B | WDG, WP |
| COMPOUND C | WDG, WP, EC |
| COMPOUND D | EC, WP, WDG |

EO = average number of ethylene oxide units
Code  Description of formulation code

| | |
|---|---|
| DF | dry flowable |
| EC | emulsifiable concentrate |
| EW | water in oil emulsions |
| FL | flowable |
| FS | flowable concentrate for seed treatment |
| GR | granules |
| L | liquid |
| OF | oil miscible flowable concentrate |
| SC | suspension concentrate |
| WDG | wettable dispersible granules |
| WP | wettable powder |
| WS | water dispersible powder for slurry treatment |

TABLE 6

Structures for Compounds A to D:

Structure

COMPOUND A

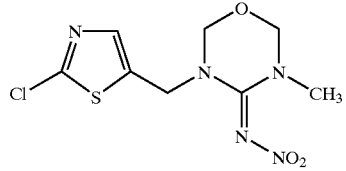

COMPOUND B

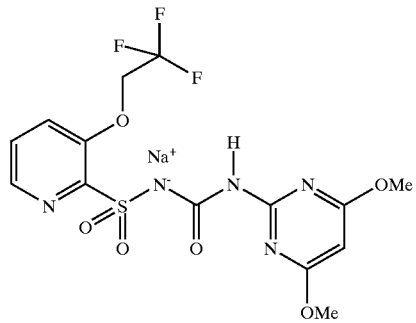

COMPOUND C

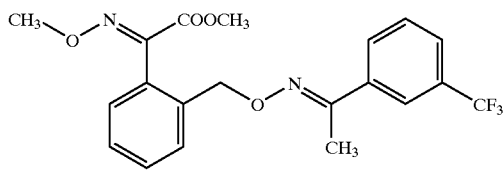

COMPOUND D

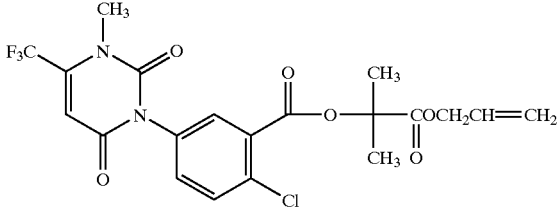

In summary, it is seen that this invention provides new compounds useful as surfactants that are alternatives to known or conventional surfactant systems. In particular, the surfactants compounds of the instant invention are useful for formulating agrochemical compositions. Variations may be made in proportions, procedures and materials without departing from the scope of the invention as defined by the following claims.

What is claimed is:

1. A compound of the formula (H-B)$^+$A$^-$ wherein A$^-$ is:

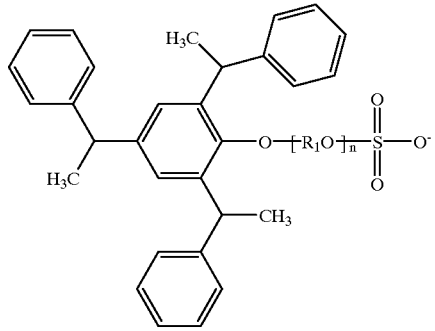

wherein each $R_1$ independently is a straight chain or branched $C_2$-$C_4$ alkylene, n is a number from 1 to 50 inclusive,
wherein (H-B)$^+$ is the cation of the formula:

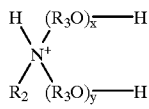

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive.

2. A compound according to claim 1, wherein A$^-$ is:

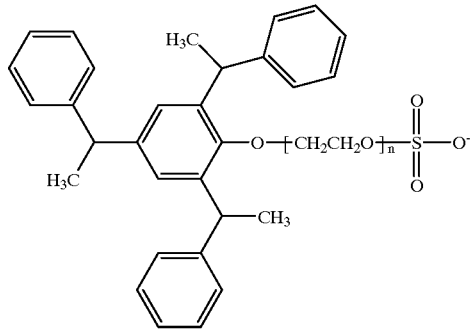

and wherein (H-B)$^+$ is the cation of the formula:

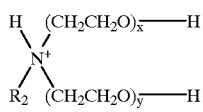

wherein x+y is a number from about 4 to 9.

3. A compound according to claim 2, wherein n is 4 to 16.
4. A compound according to claim 3, wherein n is 8.
5. A compound according to claim 4, wherein $R_2$ is selected from the group consisting of n-octadecyl, n-hexadecyl and cis-9-octadecenyl; and x+y is equal to 5.
6. A product obtained by the process of neutralizing at least one aromatic acid of formula (2):

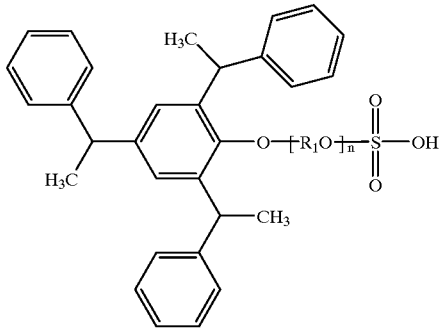

wherein each $R_1$ independently is a straight chain or branched $C_2$-$C_4$ alkylene, n is a number from 1 to 50 inclusive,
with at least one alkoxylated amine base of formula (3):

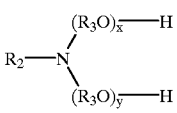

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive.

7. A product according to claim 6, where said at least one aromatic acid is a compound defined by the formula (2a):

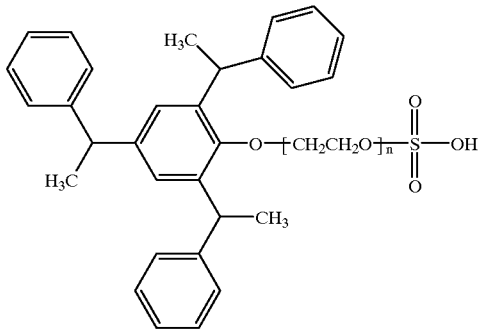

and wherein said at least one ethoxylated amine base is a compound defined by the formula (3a):

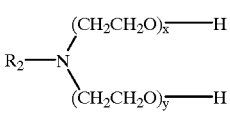

wherein $R_2$ is $C_1$-$C_{24}$ alkyl and the average of x+y is a number from about 4 to 9.

8. A product according to claim 6, wherein the product has a pH of about 3 to 9.

9. A product according to claim 6, wherein the product has a pH of about 3 to 8.5.

10. A product according to claim 6, wherein the product has a pH of 5 to 8.

11. A surfactant composition comprising a salt of:

(a) at least one aromatic acid is a compound of the formula (2):

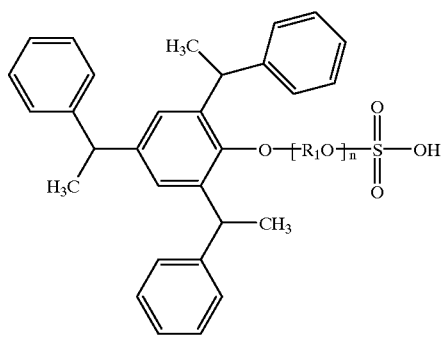

(2)

wherein each $R_1$ independently is a straight chain or branched $C_2$-$C_4$ alkylene, n is a number from 1 to 50 inclusive; and (b) at least one alkoxylated amine base of the formula (3):

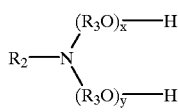

(3)

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive.

12. A surfactant composition according to claim 11 wherein:

(a) is at least one aromatic acid compound of the formula (2a):

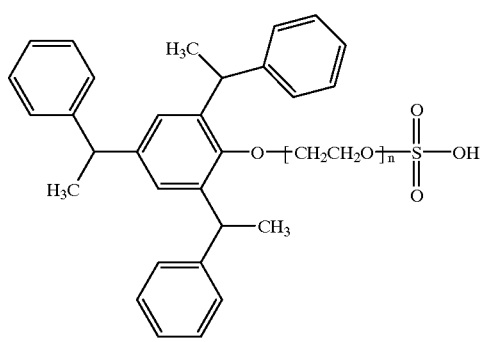

(2a)

and (b) is at least one ethoxylated amine base of the formula (3a):

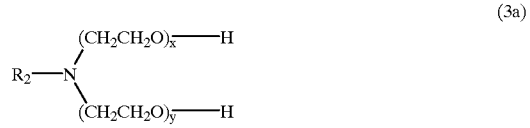

(3a)

wherein $R_2$ is $C_1$-$C_{24}$ alkyl and the average of x+y is a number from about 4 to 9.

13. A composition of claim 11, wherein the surfactant composition has a pH of about 3 to 9.

14. A composition of claim 11, wherein the surfactant composition has a pH of about 3 to 8.5.

15. A composition of claim 11, wherein the surfactant composition has a pH of 5 to 8.

16. A chemically integrated surfactant composition comprising at least one aromatic acid compound of formula (2):

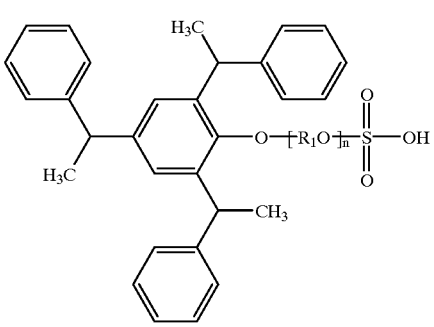

(2)

wherein each $R_1$ independently is a straight chain or branched $C_2$-$C_4$ alkylene, n is a number from 1 to 50 inclusive, and at least one alkoxylated amine base of the formula (3):

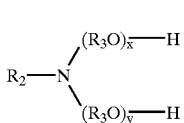

(3)

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive, or the chemical interaction products thereof.

17. A chemically integrated surfactant composition according to claim 16 where the aromatic acid is at least one compound of the formula (2a):

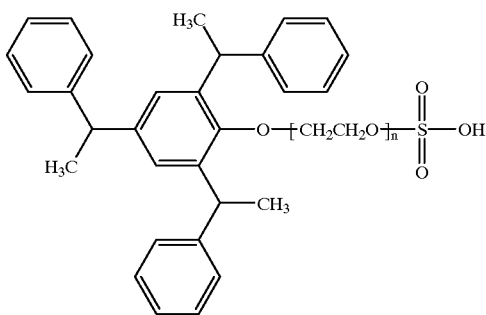

(2a)

and at least one ethoxylated amine base is a compound defined by the formula (3a):

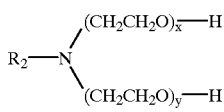

(3a)

wherein $R_2$ is $C_1$-$C_{24}$ alkyl and the average of x+y is a number from about 4 to 9.

18. A composition of claim 16, wherein the surfactant composition has a pH of about 3 to 9.

19. A composition of claim 16, wherein the surfactant composition has a pH of about 3 to 8.5.

20. A composition of claim 16, wherein the surfactant composition has a pH of 5 to 8.

21. A pesticide formulation comprising at least one pesticide and at least one aromatic acid neutralized with at least one ethoxylated amine wherein said aromatic acid is of the formula (2):

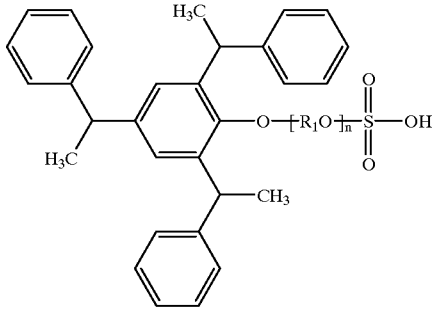

(2)

wherein each $R_1$ independently is a straight chain or branched $C_2$-$C_4$ alkylene, n is a number from 1 to 50 inclusive,
and the said alkoxylated amine is of the formula (3):

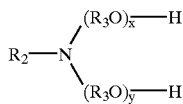

(3)

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive.

22. A pesticide formulation according to claim 21 wherein said aromatic acid is of the formula (2a):

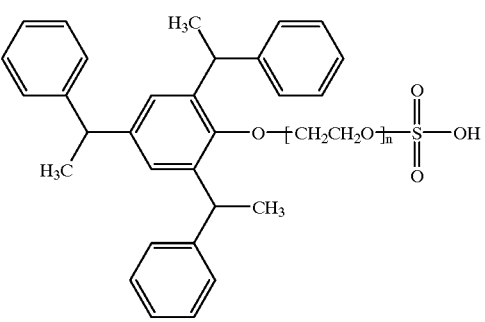

(2a)

and the said ethoxylated amine is of the formula (3a):

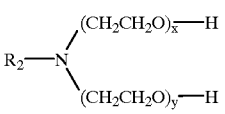

(3a)

wherein $R_2$ is $C_1$-$C_{24}$ alkyl and the average of x+y is a number from about 4 to 9.

23. A pesticide formulation of claim 21 wherein the pesticide is atrazine or glyphosate.

24. A method of protecting crops comprising the step of applying to the locus of the crops in need of protection an agriculturally effective amount of the formulation of claim 21.

25. A method of protecting crops comprising the step of applying to the locus of the crops in need of protection an agriculturally effective amount of the formulation of claim 22.

26. A method of using the compound of claim 1 as an alternative surfactant which comprises substituting a known alkylphenol ethoxylate surfactant system in a formulation with the compounds having the formula $(H\text{-}B)^+A^-$.

27. A compound of Formula (1):

$$(H\text{-}B)^+A^- \qquad (1)$$

wherein $A^-$ is the conjugate base of the acid H-A, wherein H-A is an alkoxylated tristyrylphenol hemi-sulfate ester; and the $(H\text{-}B)^+$ is the conjugate acid of the base B, wherein B is an alkoxylated amine of the formula (3)

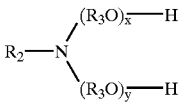

(3)

wherein $R_2$ is selected from the group consisting of $C_1$-$C_{24}$ alkyl and $C_2$-$C_{24}$ alkenyl-$CH_2$-, each $R_3$ independently is a straight chain or branched $C_2$-$C_4$ alkylene, x is a number from 1 to 50 inclusive and y is a number from 0 to 50 inclusive.

* * * * *